(12) United States Patent
Bates (10) Patent No.: US 6,796,937 B1
(45) Date of Patent: Sep. 28, 2004

(54) UNIPOLAR BIOMAGNETIC THERAPY APPLIANCE

(76) Inventor: Kerry M. Bates, 2901 NW. 16th, Newcastle, OK (US) 73065

( * ) Notice: Subject to any disclaimer, the term of this patent is extended or adjusted under 35 U.S.C. 154(b) by 0 days.

(21) Appl. No.: 10/696,861

(22) Filed: Oct. 30, 2003

(51) Int. Cl.[7] ................................................ A61N 1/00
(52) U.S. Cl. ......................................................... 600/15
(58) Field of Search ...................................... 600/9–15

(56) References Cited

U.S. PATENT DOCUMENTS

| | | |
|---|---|---|
| 3,943,912 A | 3/1976 | Nakayama |
| 4,095,587 A | 6/1978 | Ishikawa |
| 5,707,333 A | 1/1998 | Bakst |
| 6,375,324 B2 | 4/2002 | Schleger et al. |
| 6,558,310 B1 | 5/2003 | Baermann et al. |
| 2002/0104151 A1 | 8/2002 | Rauscher |
| 2002/0133219 A1 | 9/2002 | Barry |
| 2002/0143231 A1 | 10/2002 | Kulish |
| 2002/0198433 A1 | 12/2002 | Roberts et al. |
| 2002/0198435 A1 | 12/2002 | Paturu |
| 2003/0004393 A1 | 1/2003 | Ewing et al. |
| 2003/0045770 A1 | 3/2003 | van Mullekom |
| 2003/0163018 A1 | 8/2003 | Sexton |
| 2003/0163896 A1 | 9/2003 | Rabello |
| 2003/0195381 A1 | 10/2003 | Baermann et al. |

OTHER PUBLICATIONS

"Biomagnetic Healing" by Gary Null, 48 pages.
"Therapy Magnet History", downloaded from http://www.discovermagnetics.com on Oct. 20, 2003, 2 pages.
"Dr. Philpott Designed and Approved Polar Power Magnets", downloaded from http://azunimags.bigstep.com on Oct. 20, 2003, 2 pages.
"Welcome to our 'Magnetics Applied to Cancer' page", downloaded from http://azunimags.bigstep.com on Oct. 20, 2003, 3 pages.
"Importance of Polarity", downloaded from http://azunimags.bigstep.com on Oct. 20, 2003, 2 pages.
"How Does MME Work?", downloaded from http://www.supportsusa.com on Oct. 20, 2003, 2 pages.
"Magnetic Bioflex Supports", downloaded from http://www.supportsusa.com on Oct. 20, 2003, 4 pages.
"Biological Effects of Magnetism", downloaded from http://www.e-magnetship.com on Oct. 20, 2003, 2 pages.

*Primary Examiner*—John P. Lacyk
(74) *Attorney, Agent, or Firm*—Robert H. Frantz (57) ABSTRACT

Three steel rods are formed into a shape for a collar, necklace, anklet or belt, with one rod disposed between the other two rods. The middle rod has a larger radius of curvature than the top and bottom rods, and a plurality of rare earth magnets are placed between the middle rod and the outer rods. Each magnet is oriented such that all of the magnets have their same polar ends pointed towards the top and bottom rods. The magnets are bonded to the rods using a magnetically conductive material, to form a magnetic circuit which produces a unipolar magnetic field along the top and bottom rods towards the center of the U-shaped appliance such that the wearer of the appliance may receive unipolar biomagnetic therapeutical benefits of the magnets.

12 Claims, 6 Drawing Sheets

UNIPOLAR BIOMAGNETIC THERAPY APPLIANCE

CROSS-REFERENCE TO RELATED APPLICATIONS (CLAIMING BENEFIT UNDER 35 U.S.C. 120)

Not applicable.

FEDERALLY SPONSORED RESEARCH AND DEVELOPMENT STATEMENT

This invention was not developed in conjunction with any Federally sponsored contract.

MICROFICHE APPENDIX

Not applicable.

INCORPORATION BY REFERENCE

The following web document is incorporated herein, including its illustrations, to the present disclosure "Biological Effects of Magnetism" by E-Magnet Shop,

BACKGROUND OF THE INVENTION

1. Field of the Invention

This invention relates to the arts of biomagnetism and magnetic therapy.

2. Description of the Related Art

The field of biomagnetics and magnetic therapy is currently re-emerging as treatment for the relief of pain, discomfort and stress, for increasing circulation, and for the possible cure of many diseases in both humans and animals. Historians indicate that magnets have been used as a healing aid for thousands of years, tracing earliest known usage thousands of years. For example, "The Yellow Emperors Book of Internal Medicine", a Chinese text dating back to 2000 B.C., describes how the application of magnetic stones could correct imbalances in the 'Qi' or life force. Egyptian writings document that ancient Egyptian physicians attributed a variety of therapeutic effects to magnetism—a well-known story even states that Cleopatra regularly adorned herself with magnetic jewelry or wore a magnetic stone around her forehead to preserve her youthfulness. Other ancient civilizations known to utilize magnets for health reasons include Indian, Arabic, and Hebrew cultures. Although biomagnetic therapy's popularity has faded and reemerged many times over the centuries, the medical use of magnets has been well established.

Recent university studies confirm that the use of magnets in conjunction with traditional therapies can reduce the amount of time required for many types of wounds and injuries to heal. There is also evidence to show that magnet therapy is effective in reducing and sometimes alleviating pain and stress. Some current research supports that the topical application of permanent magnets may indeed relieve pain and inflammation.

For example, one provider of magnetic products, E-MagnetShop, states that when a therapeutic magnet is placed on the skin of a wearer, the magnetic force field penetrates the flesh and blood that passes through this magnetic force field. Using a microscope, calcium molecules prior to passing through a magnetic field can be seen to have spines and barbs, and are clumped, which can slow down circulation, and may collect on the inside of blood vessels. However, following exposure to a magnetic field, calcium molecules appear to resemble grains of rice, and are smaller than the untreated calcium molecules. The smaller, streamlined calcium molecules are believed to circulate more efficiently. Additionally, oxygen and nutrients are transported faster and toxins are carried away more quickly, according to this web-based retailer of biomagnetic properties.

A document on this company's website entitled "Biological Effects of Magnetism", also states that other tissue and blood-borne molecules are also affected after passing through a magnetic field such as minerals and hydrogen. For example, they explain that hydrogen molecules control pH, and when exposed to a biomagnetic north field, hydrogen resets pH to the proper balance, which is essential for optimum health. Dr. Burl Payne, former professor at Boston University and Goddard College and inventor-designer of biofeedback instruments, stated in his books "The Body Magnetic" and "Getting Started in Magnetic Healing", that there are now known factors to be involved in magnetic healing including:

(a) Increasing blood flow with resultant increased oxygen-carrying capacity, both of which are basic to healing the body heals itself.

(b) Changing the migration of calcium ions—adequate magnetic polarities can either bring calcium ions to heal a broken bone in half the usual time, or can help move calcium away from painful, arthritic joints.

(c) The pH balance (acid/alkaline) of various body fluids (often out of balance in conjunction with illness or abnormal conditions) can apparently be altered by magnetic fields.

(d) Hormone production from the endocrine glands (essential to health) can be either increased or decreased by magnetic stimulation.

(e) Altering of enzyme activity and other biochemical processes.

This web site goes on to describe that in a double-blind test, magnetism helped 90 percent of a large group of patients with myositis, bursitis, arthritis and rheumatism, as well as other research has shown better healing of scars. This site also states that a respected medical journal in Switzerland called "Swiss Neuropath" reports magnets are widely used to help patients with headaches including migraines, as well as constipation, bronchitis, hypertension, hemorrhoids, glaucoma and many other serious diseases. This site also quotes Dr. K. E. MaClean, M.D. of New York, as stating that cancer cannot exist in a strong magnetic field.

Many magnetic therapy products are already on the market today, such as the ones sold by E-Magnet Shop. One aspect of their design which determines their effectiveness centers around the "reach" of the magnetic field, and specifically how to provide a useful magnetic field in a topical form that will have a lasting effect within the body.

In the biomagnetic scientific community, poles on magnets used for magnetic therapy are named differently that traditional, non-medical scientific definitions. Classification of a magnetic pole in the fields of biomagnetics and magnetic therapy is based on the attraction to geographic north or south. Simply put, the end of the magnet attracted to geographic North is referred to as the "North" or the "negative" pole of the magnet, and the opposite end of the magnet is referred to as "South" or "positive."

Figure 1:
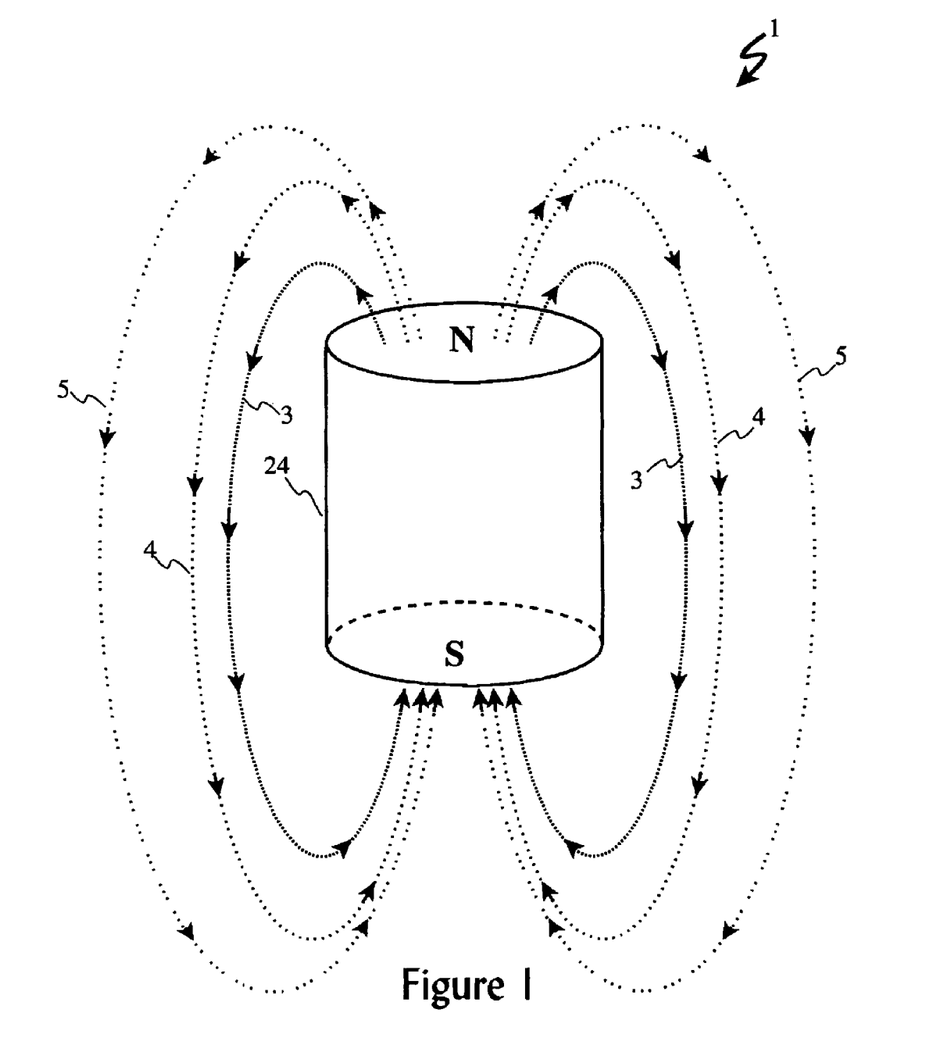
FIG. 1 shows a detailed side view of a single rare earth permanent rod magnet with the direction and strength of the magnetic field illustrated by dotted lines and arrows.

FIG. 1 depicts the magnetic field (1) created by a standard, circular rod magnet (24) with conventional biomagnetic north and biomagnetic south labels. As the distance from the magnet is increased (3,4,5), the force of the magnetic field, or magnetic flux, reduces. The magnetic flux surrounding the rod magnet radiates circumferentially and symmetrically around the axis of the cylinder which the rod magnet represents, although FIG. 1 only shows the flux in a single plane corresponding to the sheet of paper on which the figure is printed. The theory of magnetic therapy is centered around the actual magnetic field, thus, the size of and tissue proximity to the magnet creating the field.

In a topical application, such as magnetic therapy, there exists a need for an easy, portable way to apply a magnetic field to the body without restricting movement or activity. Many products exist on the market utilizing magnetic therapy in semi-permanent forms such as mattress pads with magnets embedded in them, bulky magnetic "belts" which must be strapped around the torso or an appendage, or large, flat magnets which are placed on the body while the user remains immobile.

Existing solutions, such as magnetized mattress pads, belts, wraps (e.g. elbow, ankle, torso, knee, etc.), and beaded necklaces provide magnets which are attached directly to the body, utilizing bipolar or multipolar fields to magnetize blood cells as the blood passes through the magnetic fields. For example, a mattress pad cover has a set of magnets arranged in a grid or checker board pattern, with alternating positive and negative poles facing upwards towards the person undergoing the therapy.

These types of devices typically inhibit the movement and activity level of the wearer or user, and they do not provide a unipolar field, and therefore, do not control the polarity of each blood cell. Rather, these methods rely on the idea of continually changing the polarity of blood cells and molecules in the blood stream as they pass through the alternating magnetic fields to provide relief within the body. Additionally, these types of devices provide a large area of magnetization, which may or may not be beneficial in some circumstances, and which may cause the appliance to be uncomfortable.

According to another biomagnetic appliance producer Arizona Unipolar Magnetics, William H. Philpott, M.D. has identified certain advantages to applying a unipolar magnetic field for certain therapeutical purposes. For example, Dr. Philpott has determined that application of just the biomagnetic north field to tissue and blood may have beneficial effects including increasing cellular oxygen, reducing fluid retention, promoting better sleep, fighting infection, promoting mental acuity, reducing inflammation and pain, as well as dissolving fatty deposits and calcium deposits. The unipolar biomagnetic therapy appliances produced and sold by Arizona Unipolar Magnetics include their "Sta-tight"™ wraps, Mega-Field™ mattress pads, and belts and straps. These appliances can be cumbersome to install or put on, and may also provide comfort problems (sweating, circulation restriction), and inhibition of movement of the wearer. Many of these products also provide a large area of magnetic field immersion, rather than a spot or localized application of magnetic fields.

Another technology currently being employed by medical professionals is known as Magnetic Molecular Energizing, or MME for short, developed by Dr. Dean Bonile in 1990. MME is related in operation to the better known Magnetic Resonance Imaging, or MRI. MRI, however, is directed towards imaging tissues, where MME is directed towards therapeutical benefits of applying a high Gauss field (e.g. 5,000 Gauss) to portions of a patient's body. This treatment system, however, is fairly large resembling a full-body X-ray or MRI system having a bed disposed between two very large magnets. This requires the patient to visit a physician's office or clinic periodically to receive the treatments, and thus does not allow for continual and convenient application of the magnetic fields to the desired body area.

Therefore, there exists a need in the art for a portable, easy to wear and unobtrusive method of delivering a single polarity magnetic field to a spot location of a wearer's body, especially to appendages such as the neck, arms, and legs.

SUMMARY OF THE INVENTION

The present invention provides a topical, localized or spot application of unipolar (e.g. primarily north or primary south fields) magnetic field to a portion of a wearer's body through a configuration of magnets in a necklace, bracelet, anklet, or belt Steel components of the device hold a set of magnets so as to expose the wearer to only one field of the magnets, and diffuses the magnetic field through magnetic conduction in between the magnets in order to provide a more even exposure to field strength.

In a preferred embodiment, the present invention comprises a generally horseshoe-shaped appliance with rare earth magnets spaced between a set of three metal rods, with the magnets spaced and tilted in such a way that a uniform unipolar magnetic field is diffused along the rods and directed inward toward the user.

This diffused, unipolar field radiates to tissue and blood flowing through the horseshoe-shaped appliance. The entirety of the present invention is preferably contained within a protective covering for added comfort and decoration for the user.

The horseshoe configuration allows the present invention to be worn around the neck of the user in a collar fashion, without limiting the mobility of the user. With alternate proportions, the present invention can be used as an anklet, bracelet, belt, or any other form which encircles a portion or extremity of the body.

Additional features and advantages of the present invention will be further understood and appreciated by those skilled in the art by reference to the following written specification, claims, and drawings.

BRIEF DESCRIPTION OF THE DRAWINGS

The figures presented herein, when taken in conjunction with the written disclosure, form a complete description of the invention.

DETAILED DESCRIPTION OF THE INVENTION

According to the publicly available literature for biomagnetics, it is believed that the north, or negative, pole of a magnet may reduce pain and swelling, increase circulation, inhibit cancer cell growth, and provide other desirable effects within the body. Therefore, our disclosure of a preferred embodiment features embodiments which concentrate the biomagnetic north or negative field towards the wearer of the appliance. It will be recognized by those skilled in the art that our structure and invention may be readily employed to focus a unipolar biomagnetic south or positive field on a portion of a wearer as well, should desirable affects for a specific application be identified. For the remainder of this disclosure, we will refer to the biomagnetic north or negative pole of our magnets simply as "north", and the biomagnetic south or positive poles simply as "south".

Figure 2:
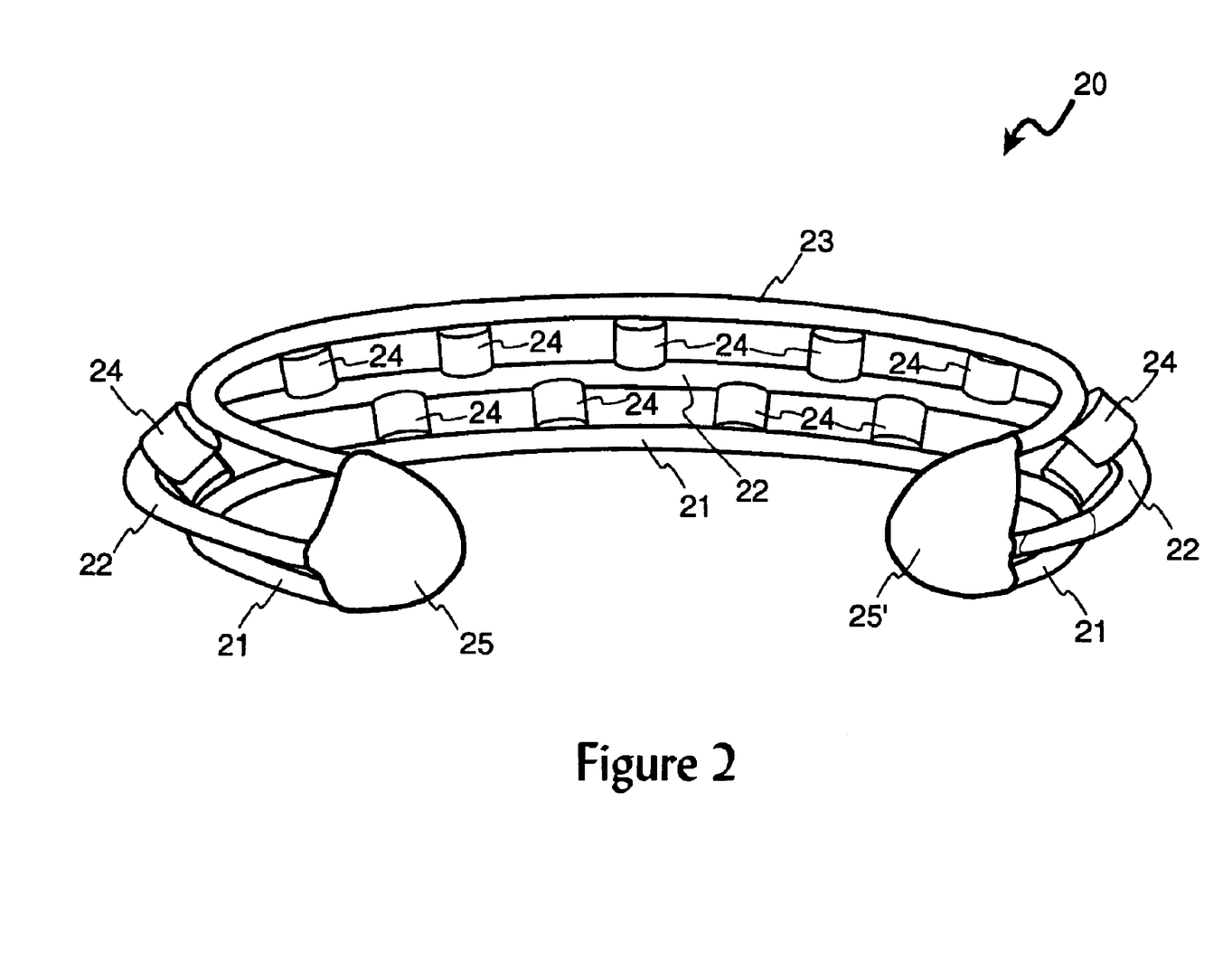
FIG. 2 provides a front perspective of the embodiment of the present invention without the protective covering.

Turning to FIG. 2, an embodiment of the invention is shown using three curved steel rods and a set of properly oriented rare earth permanent magnets spaced along the steel rods. Alternatively, a set of two horseshoe-shaped rods could be used with magnets oriented in the manner as described in the following paragraphs.

In the embodiment of FIG. 2, a bottom rod (21), middle rod (22), and top rod (23 are separately spaced and curved into a horseshoe pattern, and are brought together to meet at the ends of the horseshoe configuration (25, 25'). As will be explained in more detail in the following paragraphs, the middle rod (22) preferably has a larger radius of curvature than the top rod (23) and the bottom rod (21).

In one embodiment which demonstrated good efficacy, each rod (21, 22, and 23) was constructed from 3/16 inch diameter steel rod stock, and 15 magnets (24) are configured around the three-rod structure. The magnets (24) were commonly available permanent rare earth devices of 3500 Gauss in strength each, and were affixed to the rods (21, 22, 23) using a cold joining method, as extreme heat presented by welding or soldering may damage the magnets. Our assembly method employed a metal epoxy compound such as the well-known JB Weld™ epoxy, but other metallic joining compounds may work well, too. The ends of the rods (25, 25') may be welded, soldered, or as in our preferred embodiment, potted with JB Weld™. As will be appreciated by those skilled in the art, magnets of differing strength, different quantities of magnets, and steel rod stock different sizes can be employed to realize alternate embodiments of our invention.

Each magnet (24) is affixed at an angle with respect to the area encompassed by the appliance such that a diffused, unipolar magnetic field is produced along the steel rods (21, 22, 23) and directed toward the user. While ordinarily the field exiting the end of a rod magnet is "clumped" or concentrated near the end of the magnet, the steel rods act as magnetic conductors to diffuse the desired polar field along the top rod (23) and the bottom rod (22).

Figure 3:
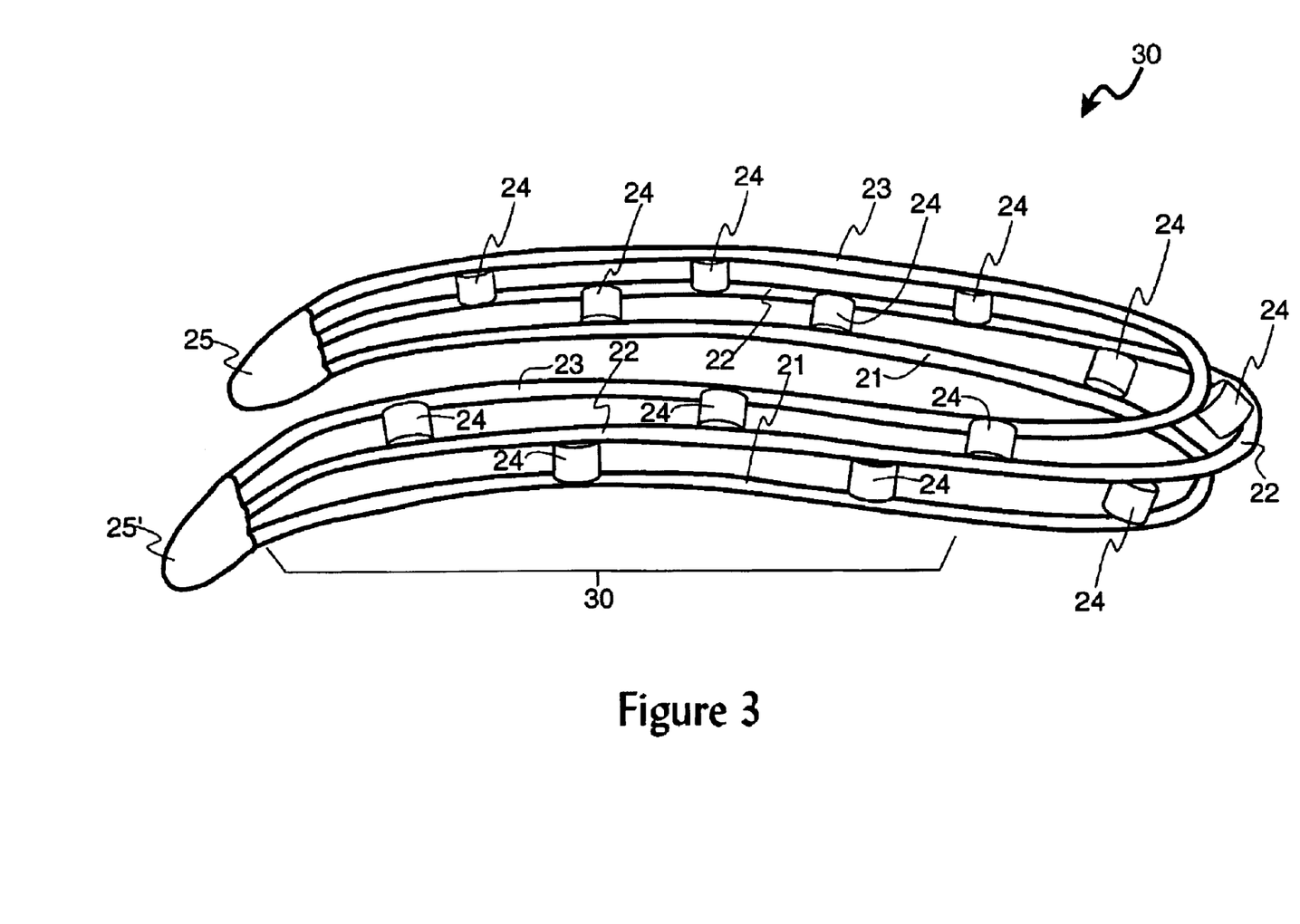
FIG. 3 illustrates a view from the left of the preferred embodiment of the present invention without the protective covering.

The left view of the appliance (30) shown in FIG. 3 provides details of a collar-style preferred embodiment, in which the sides of the rods are curved slightly downward so as to form a set of saddles (30) to receive the shoulders of a wearer. This curved shape (30) allows the appliance to rest comfortably over the shoulders of the user while holding the appliance more securely in place. Further, the curved shape (30) also provides a more visually appealing or decorative look. This saddle shape is optional for a collar configuration, and would not necessarily be beneficial for anklet, bracelet, or belt configurations.

Figure 4:
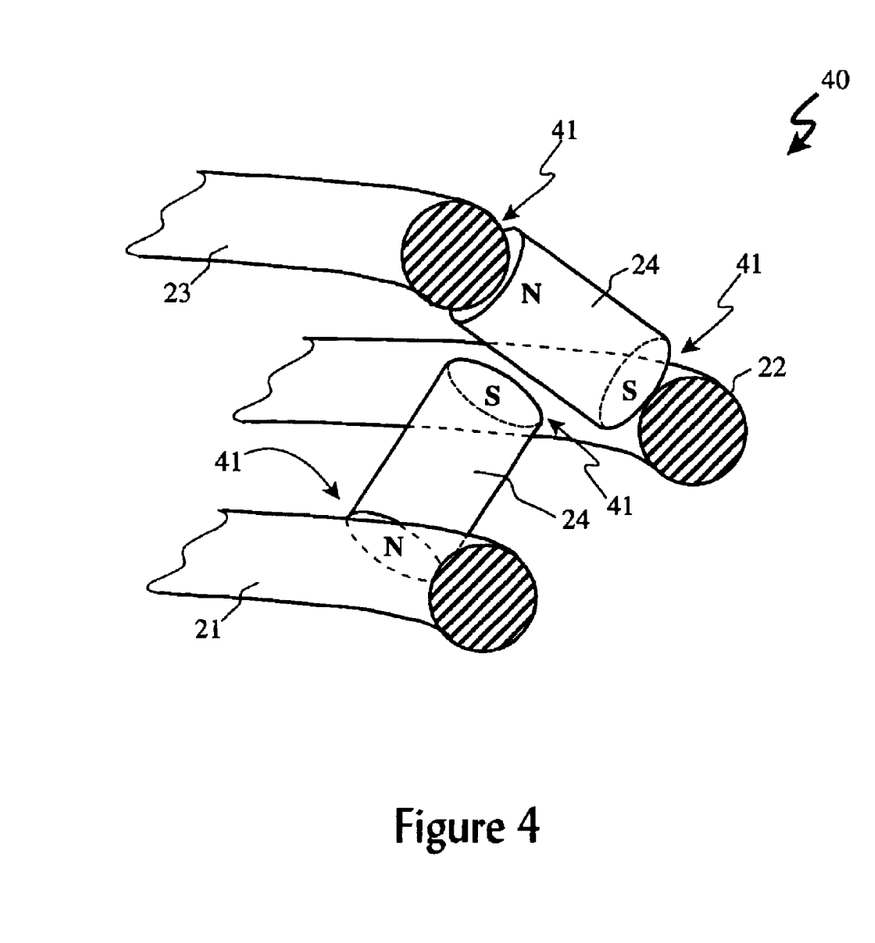
FIG. 4 depicts a cross-section view of the preferred embodiment of the present invention without the protective covering in order to illustrate the configuration of the magnets in more detail.

Turning now to FIG. 4, a cross-section view (40) of our three-rod embodiment is shown in which the angled arrangement of the magnets (24) along the steel rods (21, 22, 23) is more clearly evident. Each magnet (24) is affixed (41) to either the top rod (23) and the middle rod (22), or to the bottom rod (21) and middle rod (22), in a fashion as described in the foregoing paragraphs, such as by applying a lump of JB Weld™ epoxy (not shown) around the area where each magnet meets (41) a rod surface.

The placement and orientation of each magnet (24) is such that all the magnets have the same field ends (preferably biomagnetic negative) pointing towards the center of the appliance (e.g. affixed to the top or bottom rod), with their opposing field ends pointing towards the central rod (22). In our preferred embodiment, a diffused unipolar magnetic north field is directed toward the user along the top rod (23) and bottom rod (21), and the opposite unipolar magnetic field (S) is directed away from the user along the middle rod (22). In alternate embodiments, the orientation of each magnet may be reduced so as to produce a diffused south field towards the user.

Further according to our preferred embodiment, the entire structure is encased in any type of protective covering such as a vinyl or foam sleeve for an added level of comfort for the user, as well as to provide a more decorative look and to protect the structure from accidental damage.

Figure 5:
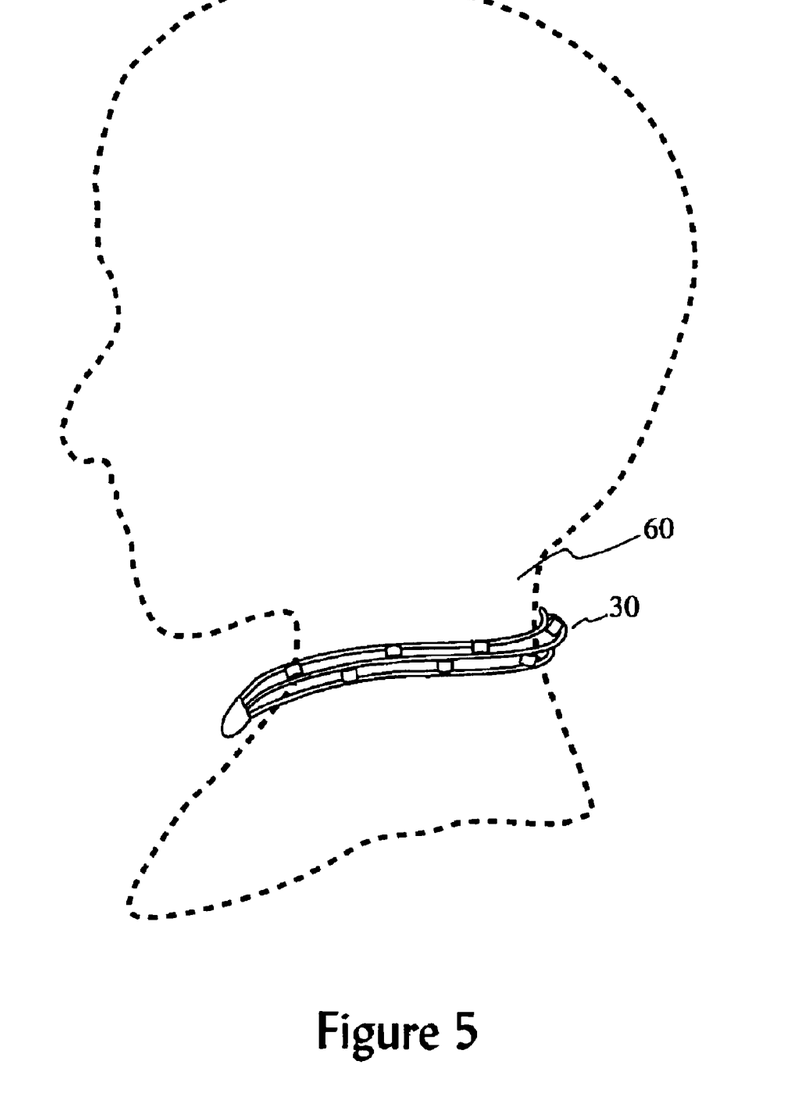
FIG. 5 illustrates how the collar embodiment of the present invention is worn around the neck of a wearer.

FIG. 5 illustrates how the preferred embodiment of a collar with saddle (30) is worn around the neck (60) of a wearer. It is easily slipped onto the neck by placing the appliance in a position behind the neck with the opening of the U-shape towards the neck, passing the unit forwards until it encompasses the neck, and then resting it onto the shoulders. Alternate embodiments for necklaces, anklets, and belts may be used similarly.

Figure 6:
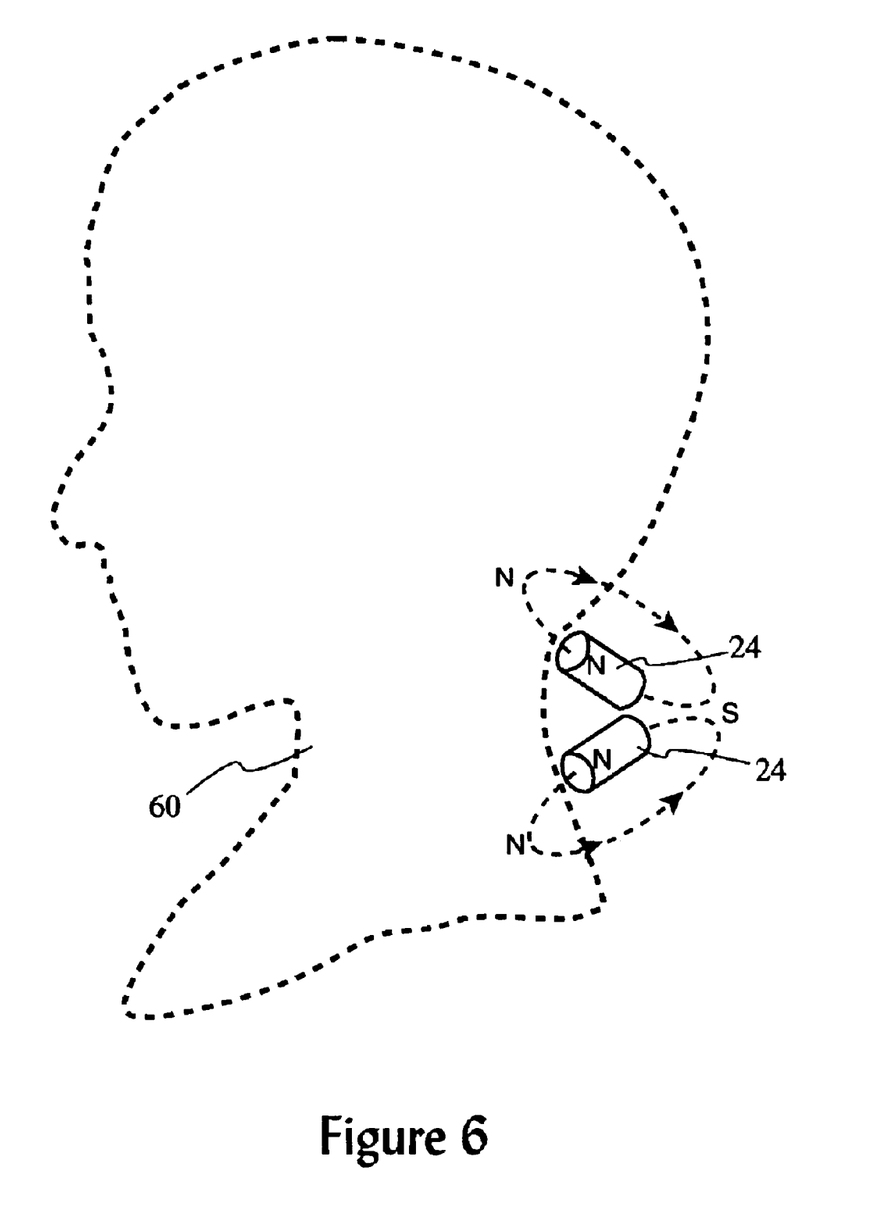
FIG. 6 shows the diffusion of the magnetic field when the present invention is worn around the neck of the user.

Turning to FIG. 6, the unipolar magnetic fields are shown directed towards the wearer's neck (60) from the ends of the magnets (24), without the rods being shown in order to provide a clearer depiction of the magnetic field arrangement of the invention. As can be seen from this illustration, the opposing field (in this case the biomagnetic south poles) of the magnets are all pointed away from the neck (60) such that tissue and blood flowing through the neck are subjected to only one pole (in this example north) of the magnets, not both poles. As such, blood and tissue exposed only to one pole, and not to multiple poles or alternating poles as in the existing products. It is also evident from this figure that the area of the wearer which is subjected to the unipolar magnetic field is a "spot location" or ring around the neck, instead of being a large area being produced by a sheet or grid array of magnetics. This improves the user's comfort level (e.g. minimizes skin contact with the appliance) and the user's ability to move while wearing the appliance, but still maintains the benefits to the entire body of the magnetic therapy as the blood flowing through the neck and field subsequently will flow to the rest of the wearer's body.

The present invention has been disclosed in general terms as well as with specific examples and descriptive illustrations. It will be recognized by those skilled in the art that the scope of the present invention is not limited to these illustrations and examples, and that the present invention may be realized in a number of alternate forms, and constructed of a variety of alternate materials.

Certain details of preferred embodiments have been described, but it will be recognized by those skilled in the art that many substitutions and variations may be made from the disclosed embodiments without departing from the spirit and scope of the invention. Therefore, the scope of the invention should be determined by the following claims.

What is claimed is:

1. A device for applying a localized, diffused unipolar magnetic field to a portion of a wearer's body comprising:
   a first and a second magnetically conductive rods shaped generally in a U-shape, and proportioned to be received around a body portion, said rods being affixed at their ends to form a complete magnetic circuit, said second rod having a greater radius of curvature than said first rod;
   a plurality of magnets spaced along said rods, each magnet having a first polarity end and a second polarity end, all of said magnets being oriented such that said first polarity ends are pointed towards said first rod and said second polarity ends are pointed towards said second rod; and
   a magnetically conductive joint formed between said magnet ends and said rods thereby affixing said magnets to said rods, and allowing said rods to conduct magnetic flux from said first polarity ends to said second polarity ends via said magnetic circuit, thereby producing a unipolar magnetic field towards a user disposed within said device.

2. The device as set forth in claim 1 wherein said plurality of magnets comprise between 12 and 18 magnets of about 3500 Gauss each.

3. The device as set forth in claim 1 said first polarity ends are biomagnetic positive ends.

4. The device as set forth in claim 1 said first polarity ends are biomagnetic negative ends.

5. The device as set forth in claim 1 wherein said first and second rods are proportioned to be worn as a collar on a wearer.

6. The device as set forth in claim 1 wherein said first and second rods are proportioned to be worn as a bracelet on a wearer.

7. The device as set forth in claim 1 wherein said first and second rods are proportioned to be worn as a anklet on a wearer.

8. The device as set forth in claim 1 wherein said first and second rods are proportioned to be worn as a belt on a wearer.

9. The device as set forth in claim 1 wherein said first and second rods are further shaped to form a saddle for receiving and nestling onto shoulders of a wearer.

10. The device as set forth in claim 1 further comprising a third U-shaped rod similarly proportioned to said first rod, arranged juxtaposed to said first rod with said second rod disposed therebetween, and having a plurality of magnets affixed between said third rod and said second rod such that said magnets oriented with their first polarity ends are pointed towards said third rod and said second polarity ends are pointed towards said second rod.

11. The device as set forth in claim 1 wherein at least one of said rods comprises a steel rod of about 3/16 inch diameter.

12. The device as set forth in claim 1 further comprising a covering disposed around said rods and magnets to provide protection for said joints and magnets, and to allow comfortable wear by a wearer.

* * * * *